(12) United States Patent
Kodama et al.

(10) Patent No.: US 11,813,090 B2
(45) Date of Patent: Nov. 14, 2023

(54) DETERMINATION DEVICE

(71) Applicants: The Ritsumeikan Trust, Kyoto (JP); Kumagai Gumi Co., Ltd., Fukui (JP)

(72) Inventors: Kota Kodama, Osaka (JP); Nobuki Hashiguchi, Shiga (JP); Shigeo Kitahara, Tokyo (JP); Yasuhiro Miyazaki, Tokyo (JP)

(73) Assignees: THE RITSUMEIKAN TRUST, Kyoto (JP); KUMAGAI GUMI CO., LTD., Fukui (JP)

( * ) Notice: Subject to any disclaimer, the term of this patent is extended or adjusted under 35 U.S.C. 154(b) by 53 days.

(21) Appl. No.: 17/124,718

(22) Filed: Dec. 17, 2020

(65) Prior Publication Data

US 2021/0186432 A1 Jun. 24, 2021

(30) Foreign Application Priority Data

Dec. 18, 2019 (JP) .................. 2019-227876

(51) Int. Cl.
*A61B 5/00* (2006.01)
*A61B 5/024* (2006.01)
(Continued)

(52) U.S. Cl.
CPC ............ *A61B 5/7275* (2013.01); *A61B 5/024* (2013.01); *A61B 5/1118* (2013.01); *A61B 5/6801* (2013.01); *A61B 2503/20* (2013.01)

(58) Field of Classification Search
CPC ........ A61B 2503/20; A61B 2562/0219; A61B 5/0022; A61B 5/024; A61B 5/0245; A61B 5/1118; A61B 5/6801; A61B 5/6805; A61B 5/681; A61B 5/7264; A61B 5/7275; A61B 5/746; G16H 50/00–50/80
See application file for complete search history.

(56) References Cited

U.S. PATENT DOCUMENTS

2008/0281633 A1* 11/2008 Burdea ................ A61B 5/0002
                                                          600/301
2014/0276127 A1*  9/2014 Ferdosi ............... A61B 5/0205
                                                          600/483
(Continued)

FOREIGN PATENT DOCUMENTS

JP        2017-029692 A      2/2017

*Primary Examiner* — Jonathan T Kuo
*Assistant Examiner* — Vynn V Huh
(74) *Attorney, Agent, or Firm* — McClure, Qualey & Rodack, LLP (57) ABSTRACT

[Object] It is an object to provide a determination device capable of determining the health risk of a laborer due to the labor load from the measured biological information only by measuring the biological information including the heart rate of the laborer.
[Solution to the problems] In order to solve the above problems, the determination device 1 according to the present invention includes a biological information acquisition unit 3 that acquires biological information including a heart rate of a laborer Wi, a model formula storage unit 4 that stores a model formula for discriminating a health risk due to a labor load based on the biological information, and a determination unit 5 that determines the health risk of the laborer Wi based on the biological information of the laborer Wi and the model formula stored in the model formula storage unit 4.

9 Claims, 3 Drawing Sheets

(51) Int. Cl.
*A61B 5/11* (2006.01)
*A61B 5/0245* (2006.01)

(56) References Cited

U.S. PATENT DOCUMENTS

| | | | |
|---|---|---|---|
| 2015/0019135 A1* | 1/2015 | Kacyvenski | A61B 5/389 |
| | | | 702/19 |
| 2015/0088006 A1* | 3/2015 | Rapoport | A61B 5/1112 |
| | | | 600/484 |
| 2017/0095670 A1* | 4/2017 | Ghaffari | G16H 20/30 |
| 2020/0113472 A1* | 4/2020 | Mandel-Portnoy | G16H 10/60 |

\* cited by examiner

DETERMINATION DEVICE

BACKGROUND OF THE INVENTION

(1) Field of the Invention

The present invention relates to a determination device for determining a health risk due to a laborer's labor load.

(2) Description of Related Art

Among the labor sites of the construction industry, mining industry, agriculture, forestry and fisheries industry, manufacturing industry, and the like, there are some sites that involve intense physical labor or labor in a harsh environment such as high temperature. In such harsh labor sites where the physical burden on a laborer is heavy, they are suffering from labor shortage in many cases, for example, because a newcomer does not come in or remain, laborers become old-age, and the number of skilled laborers decreases, and thus improving laborer productivity and safety has become an urgent issue. If laborers are overloaded by laboring long hours in a harsh environment, the health risks of laborers will increase, leading to injury and illness, serious accidents, etc. Therefore, in order to improve laborer productivity and safety, it is considered to be important to properly grasp and determine the labor load on laborers, and to manage labor so as to achieve appropriate staffing and labor hours based on that.

However, since each person has different physical abilities, even if the same work is performed, the load applied by the work differs from person to person. Therefore, it is difficult to uniformly determine the labor load based on the work content, and it is necessary to determine the labor load for each individual laborer.

Here, there is an index used for exercise intensity called the reserve heart rate (% of Heart Rate Reserve, % HRR) (hereinafter referred to as % HRR). % HRR is expressed by the following formula.

$$\% \text{ HRR} = (\text{heart rate} - \text{heart rate at rest}) \div (\text{maximum heart rate} - \text{heart rate at rest}) \times 100$$

In the above formula, the heart rate at rest is the heart rate when the person exercising is at rest without exercising, and the maximum heart rate is the maximum heart rate that the person exercising can produce. It is a constant determined by each individual. When some exercise is performed, the heart rate rises in proportion to the intensity of the exercise, and takes a value from the heart rate at rest to the maximum heart rate. % HRR is a relative index indicating, from the heart rate during exercise, how much the exercise is loaded against the limit of the person by 0 to 100%.

So far, studies have been conducted to clarify the relationship between % HRR and health risk for this % HRR. For example, in K. Norton et al., "Position statement on physical activity and exercise intensity terminology", Journal of Science and Medicine in Sport 13 (2010) p. 496-502 (Non-Patent Document 1), % HRR is classified into five categories according to the value, and the reference of how much load and how long it is possible to exercise for each category is shown. According to Non-Patent Document 1, less than 20% HRR is classified as a category of exercise intensity with little movement and less energy consumption from sitting or lying down, 20% or more and less than 40% HRR is a category of exercise intensity capable of continuing aerobic exercise that does not cause any noticeable change in a respiratory rate for at least 60 minutes, 40% or more and less than 60% HRR is a category of exercise intensity capable of continuing aerobic exercise that can continue conversation for 30 to 60 minutes, 60% or more and less than 85% HRR is a category of exercise intensity capable of continuing aerobic exercise that makes it difficult to continue conversation for 30 minutes, and 85% HRR or more is a category of exercise intensity incapable of continuing for 10 minutes. In addition, Hsin-Chieh Wu et al., "Relationship between maximum acceptable work time and physical workload", Ergonomics 45 (2002) p. 280-289 (Non-Patent Document 2) shows the relationship between RHR (Relative Heart Rate) and the limit of labor hours. Although it is RHR in Non-Patent Document 2, RHR is equivalent to % HRR. According to Non-Patent Document 2, the allowable labor hours are 4 hours when the RHR is 39%, and the allowable labor hours are 8 hours when the RHR is 24.5%. In addition, Sungjoo Hwang et al., "Wristband-type wearable health devices to measure construction workers' physical demands", Automation in construction 83 (2017) p. 330-340 (Non-Patent Document 3) describes a study in which a laborer at a construction site confirms a labor load with a permissible limit of 40% HRR that can last for 30 to 60 minutes.

On the other hand, in recent years, research and development of wearable devices have been actively carried out in various fields. Wearable devices are computer devices that can be worn by users in various forms such as wristwatch type, eyeglass type, and clothing type. Wearable devices are expected to be applied in the field of health monitoring because they are always worn by users. Conventionally, when measuring biological information such as an electrocardiogram, it is common to attach a disposable electrode to the skin of the person to be measured with a gel or adhesive tape, but when the measurement is performed during long-term continuous measurement or exercise movement, it was difficult to measure the biological information, such as discomfort or rash caused by sweating on the electrode-attached portion, or peeling of the gel or adhesive tape. In contrast to such conventional measurement of biological information, for example, JP 2017-029692 A discloses a clothing-type wearable device that has an electrode inside a clothing, comes into contact with the skin when a wearer wears the clothing without using an adhesive member such as a gel or an adhesive tape, and can measure an electrocardiogram even during an exercise operation such as walking or running. By using a wearable device as described in JP 2017-029692 A, it is possible to easily perform long-term measurement of biological information such as a heart rate and measurement during exercise.

CITATION LIST

Patent Literature

Patent Literature 1: JP 2017-029692 A

Non-Patent Literature

NON-Patent Literature 1: K. Norton et al., "Position statement on physical activity and exercise intensity terminology", Journal of Science and Medicine in Sport 13 (2010) p. 496-502

NON-Patent Literature 2: Hsin-Chieh Wu et al., "Relationship between maximum acceptable work time and physical workload", Ergonomics 45 (2002) p. 280-289

NON-Patent Literature 3: Sungjoo Hwang et al., "Wristband-type wearable health devices to measure construction workers' physical demands", Automation in construction 83 (2017) p. 330-340

SUMMARY OF THE INVENTION

Technical Problems

As described above, by using % HRR, it is possible to estimate the labor load tailored to each laborer rather than the uniform labor load depending on the labor content, and by applying the reference between % HRR and a health risk as described in Non-Patent Documents 1 to 3, for example, it is determined that there is a health risk if the % HRR exceeds 40%, and thus it is thought that it is possible to determine the health risk by the labor load tailored to the laborer. In addition, by using a wearable device as described in JP 2017-029692 A, a laborer can measure biological information such as a heart rate even during labor without interrupting labor, and % HRR is calculated from the heart rate, and therefore, it is considered possible to determine the labor load in real time.

However, the heart rate at rest and maximum heart rate value used in % HRR are different depending on individual laborers, so in order to obtain % HRR, data on the heart rate at rest and maximum heart rate of each laborer is required. Therefore, for example, when the health risk of a large number of laborers due to the labor load is determined at a large-scale construction site, it takes a considerable amount of time and effort to measure data of the heart rate at rest and the maximum heart rate of all the laborers in advance, the number of pieces of the data is also enormous, and it is also difficult to manage data for associating the data of heart rate at rest and maximum heart rate of each laborer prepared in advance with the data of heart rate of each laborer measured during labor and also difficult to manage the biological information measuring device and the like.

The present invention has been made in view of the above circumstances, and has an object to provide a determination device capable of determining the health risk of a laborer due to the labor load from the measured biological information only by measuring the biological information including the heart rate of the laborer.

Solutions to the Problems

In order to solve the above problems, the determination device according to the present invention includes a biological information acquisition unit that acquires biological information including a heart rate of a laborer, a model formula storage unit that stores a model formula for discriminating a health risk due to a labor load based on the biological information, and a determination unit that determines the health risk of the laborer based on the biological information of the laborer and the model formula.

Preferably, the determination device according to the present invention is characterized in that the model formula is calculated by logistic regression of known sample data.

Preferably, the determination device according to the present invention is characterized in that the biological information further includes an amount of physical activity of the laborer.

Preferably, the determination device according to the present invention is characterized in that it includes a wearable device worn on the laborer's body to measure the biological information of the laborer, and the biological information acquisition unit acquires the biological information from the wearable device.

Advantageous Effects of Invention

The determination device according to the present invention includes a biological information acquisition unit that acquires biological information including a laborer's heart rate, a model formula storage unit that stores a model formula for discriminating a health risk due to a labor load based on the biological information, and a determination unit that determines the health risk of the laborer based on the biological information of the laborer and the model formula. Therefore, according to the determination device according to the present invention, since the determination unit determines the health risk due to the labor load of the laborer based on the model formula stored in the model formula storage unit from the biological information including the laborer's heart rate acquired by the biological information acquisition unit, by simply measuring biological information of a laborer, it is possible to determine the health risk due to the labor load of the laborer without making any other measurement in advance for the laborer.

Preferably, since the determination device according to the present invention is characterized in that the model formula is calculated by logistic regression of known sample data, when a model formula that directly estimates the labor load by single regression analysis or multiple regression analysis is used, the solution by the model formula may be negative, but the solution by the model formula calculated by logistic regression always falls between 0 and 1, so it is possible to improve the accuracy of determining the health risk due to the labor load of the laborer.

Preferably, since the determination device according to the present invention is characterized in that the biological information further includes the amount of physical activity of the laborer, it is possible to improve the accuracy of determining the health risk due to the labor load of the laborer.

Preferably, since the determination device according to the present invention includes a wearable device that is worn on the laborer's body to measure the biological information of the laborer, and the biological information acquisition unit acquires the biological information from the wearable device, the wearable device allows the laborer to measure the biological information during labor of the laborer without interrupting the labor for the measurement of the biological information, and the health risk can be determined in real time.

DETAILED DESCRIPTION OF PREFERRED EMBODIMENTS

An embodiment of the determination device according to the present invention will be described below with reference to the drawings. However, the following is merely an example of an embodiment of the present invention, and the scope of the present invention is not limited to the following embodiments, and can be appropriately changed without departing from the idea of the present invention.

Figure 1:
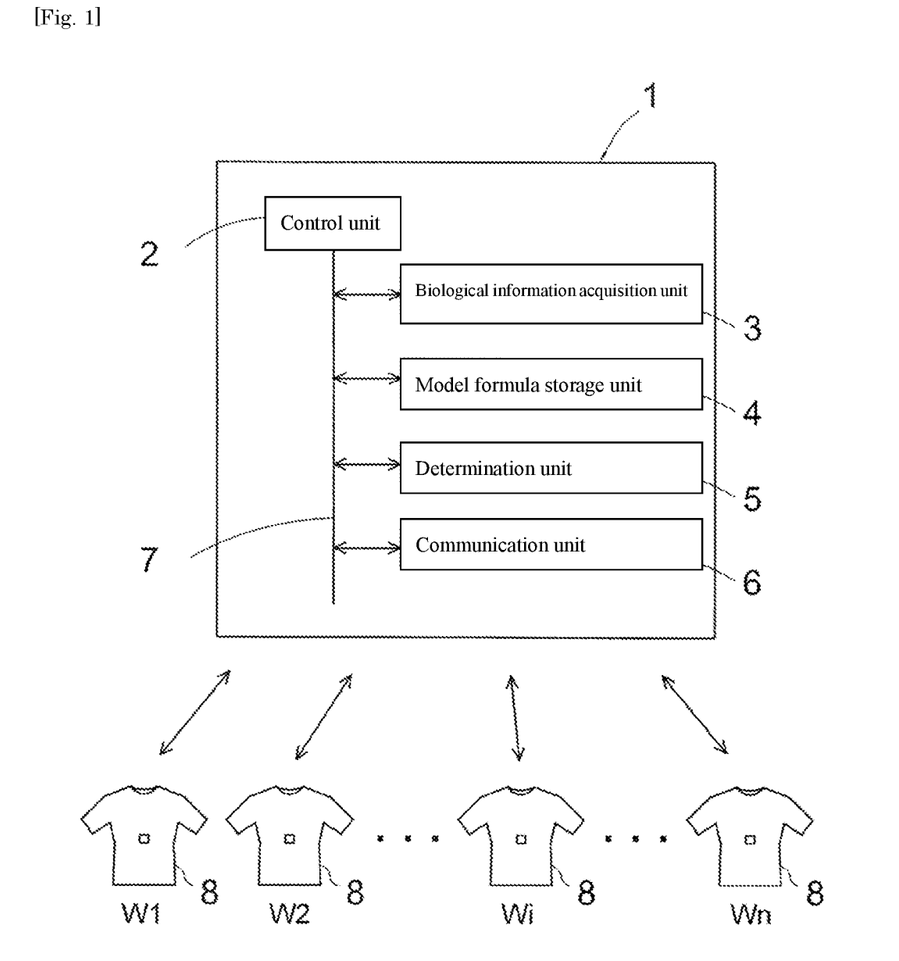
FIG. 1 is a functional block diagram of a determination device according to an embodiment of the present invention.

As shown in FIG. 1, a determination device 1 according to an embodiment of the present invention includes a control unit 2, a biological information acquisition unit 3, a model formula storage unit 4, a determination unit 5, and a communication unit 6, each of which is configured to be able to communicate various data with each other via a bus 7. In addition, each laborer Wi ($1 \leq i \leq n$) from a laborer W1 to a laborer Wn is equipped with a wearable device 8, and the determination device 1 and each wearable device 8 are connected to each other so as to be communicable.

The control unit 2 controls the determination device 1. The functions of the components of the biological information acquisition unit 3, the model formula storage unit 4, the determination unit 5, and the communication unit 6 included in the determination device 1 are executed under the control of the control unit 2. The determination device 1 can be configured by using a general-purpose computer which includes, for example, a CPU, a memory, and an input/output unit, and in which various devices such as a storage device such as an HDD and an input/output device such as a keyboard and a display can be connected to the input/output unit, and the CPU applies arithmetic processing to various programs stored in the memory to perform various functions and controls according to the programs. In that case, it may be configured so as to execute the functions of various components of the determination device 1 by configuring the CPU and memory as the control unit 2, storing programs to which the CPU applies arithmetic processing to execute the functions of the respective components of the determination device 1, and connecting various devices such as a storage device necessary for executing the functions of the respective components of the determination device 1 to the input/output unit.

The biological information acquisition unit 3 acquires biological information of each laborer Wi. The biological information acquired by the biological information acquisition unit 3 includes at least the heart rate. In the present embodiment, the biological information acquisition unit 3 acquires the amount of physical activity of each laborer Wi as biological information in addition to the heart rate of each laborer Wi.

The model formula storage unit 4 stores a model formula for discriminating the health risk due to the labor load based on biological information. The model formula storage unit 4 can be configured by using a general storage device that can read and write various data such as an HDD (Hard Disc Drive), an SSD (Solid State Drive), and a flash memory.

The determination unit 5 determines the health risk of each laborer Wi based on the biological information of each laborer Wi acquired by the biological information acquisition unit 3 and the model formula stored in the model formula storage unit 4.

The communication unit 6 wirelessly communicates various data with an external device. The communication unit 6 can be configured, for example, by using a wireless communication device conforming to a general wireless communication standard such as a wireless LAN or a mobile phone channel. In the present embodiment, as shown in FIG. 1, each laborer Wi is equipped with a wearable device 8, and the determination device 1 and each wearable device 8 are communicably connected to each other. The connection between the determination device 1 and each wearable device 8 is a wireless connection via the communication unit 6.

Figure 2:
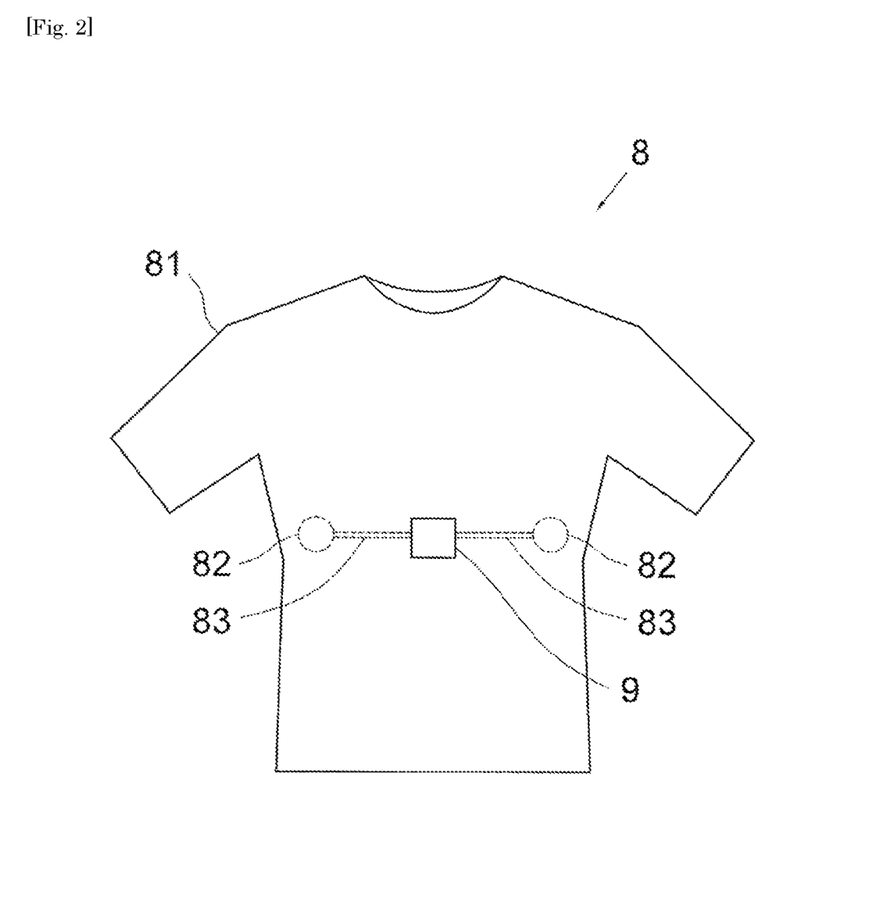
FIG. 2 is a schematic block diagram a wearable device of the determination device according to an embodiment of the present invention.

As shown in FIG. 2, the wearable device 8 includes a wear 81 worn on the upper body of the laborer Wi, two electrodes 82 and wiring 83, and a measuring device 9. The electrodes 82, wiring 83 and measuring device 9 are attached to the wear 81.

The wear 81 is a clothing that covers the trunk of the upper body of the laborer Wi when worn by the laborer Wi, directly touches the body of the laborer Wi, and adheres tightly to the body of the laborer Wi, and is formed of a highly elastic material so that it can follow the movement of the laborer Wi.

The two electrodes 82 are attached to the back side of the wear 81 so that when the laborer Wi wears the wear 81, the two electrodes 82 abut on the body surface at the left and right positions of the chest of the laborer Wi. The positional relationship is such that the heart of the laborer Wi is sandwiched between the two electrodes 82, and thus from the electrical signals acquired by the two electrodes 82, the state of the electrical activity of the heart of the laborer Wi can be observed. The electrode 82 is a dry electrode, and is not attached to the body surface of the laborer Wi using an adhesive member such as gel or adhesive tape, but when the wear 81 is brought into close contact with the body of the laborer Wi, the electrode 82 fixed to the wear 81 also comes into contact with the body of the laborer Wi. Therefore, even if it is worn for a long time, skin irritation and discomfort are less likely to occur. The electrode 82 comes into contact with the body of the laborer Wi by the wear 81 coming into close contact with the body of the laborer Wi. Therefore, it is preferable that the electrode 82 is formed of a material having stretchability so as to expand and contract following the expansion and contraction of the wear 81 due to the body movement of the laborer Wi, and having conductivity so as to be able to acquire an electric signal even during expansion.

The wiring 83 is fixed to the wear 81 and connects the electrode 82 and the measuring device 9. The electric signal acquired by the electrode 82 is sent to the measuring device 9 via the wiring 83. Since the wiring 83 is also fixed to the wear 81 like the electrode 82, it is preferably formed of a material having stretchability and conductivity according to the expansion and contraction of the wear 81.

The electrode 82 and the wiring 83 can be configured by using, for example, COCOMI (registered trademark) of Toyobo Co., Ltd. COCOMI (registered trademark) is a thin-film functional material with high stretchability and conductivity. It has a three-layer structure in which both sides of the conductive sheet are covered with insulating sheets, and can be easily applied to the fabric by thermocompression bonding. By applying COCOMI (registered trademark) to the back side of the wear 81 and peeling off the insulating sheet of the part used as the electrode 82 to expose the conductive sheet, it is possible to integrally form the electrode 82 and the wiring 83 by using the conductive part where the conductive sheet is exposed as the electrode 82 and the insulated portion covered with the insulating sheet as the wiring 83. When the electrode 82 and the wiring 83 are integrally formed in this way, a step or the like does not occur at the connection portion between the electrode 82 and the wiring 83, so that it is possible to reduce the possibility that the connection portion impairs comfort, or the laborer is preoccupied with the connection portion during labor.

Figure 3:
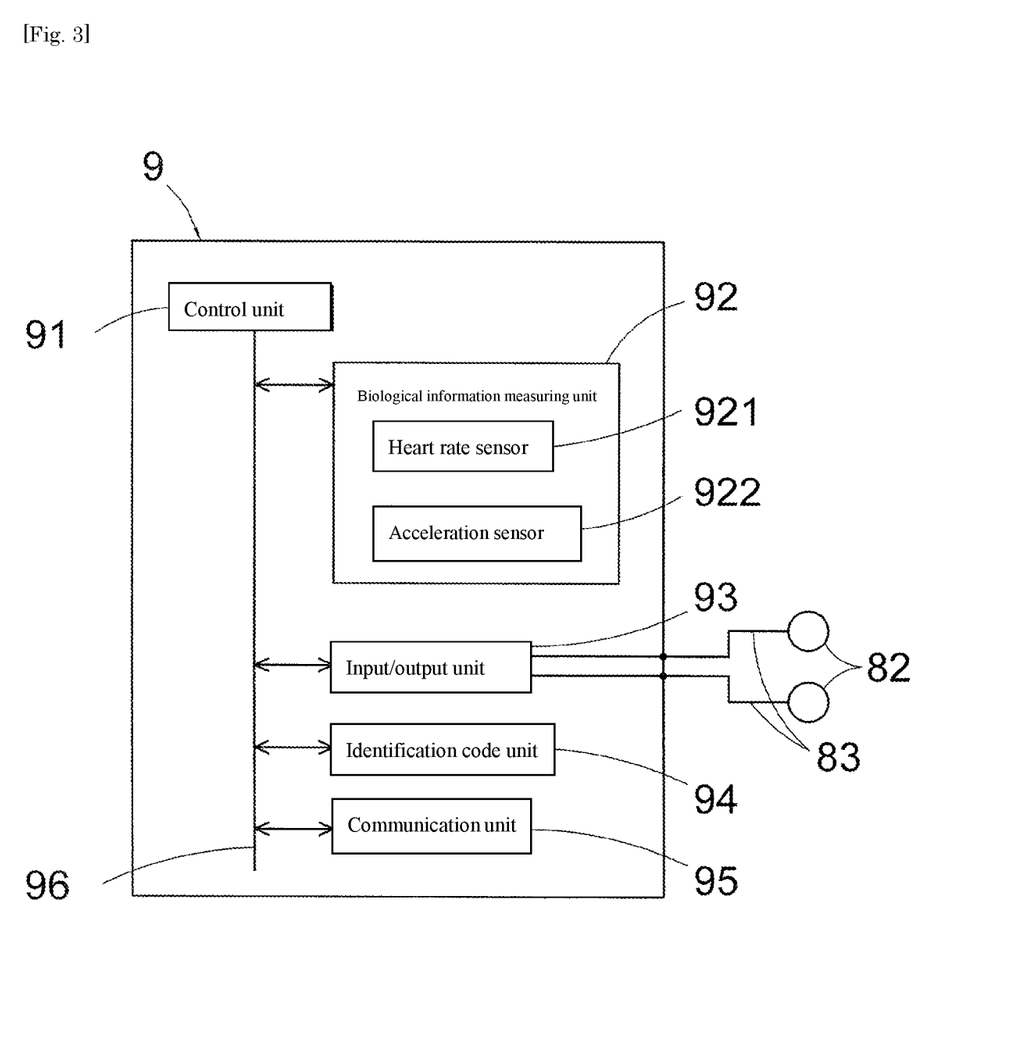
FIG. 3 is a functional block diagram of a wearable device of the determination device according to an embodiment of the present invention.

As shown in FIG. 3, the measuring device 9 includes a control unit 91, a biological information measuring unit 92, an input/output unit 93, an identification code unit 94, and a communication unit 95, each of which is configured so as to be able to communicate various data with each other via a bus 96.

The control unit 91 controls the measuring device 9. The functions of respective components of the biological information measuring unit 92, the input/output unit 93, the identification code unit 94, and the communication unit 95 included in the measuring device 9 are executed under the control of the control unit 91. The control unit 91 may be configured to include, for example, a CPU and a memory, and may be configured so that the CPU applies arithmetic processing to various programs stored in the memory to execute each function of the measuring device 9 according to the programs.

The biological information measuring unit 92 includes a heart rate sensor 921 and an acceleration sensor 922. The biological information measuring unit 92 measures the heart rate of the laborer Wi by the heart rate sensor 921, and measures the amount of physical activity of the laborer Wi by the acceleration sensor 922.

The heart rate sensor 921 measures the heart rate of the laborer Wi based on the electric signal input from the two electrodes 82 to the measuring device 9. The heart beats when the electrical signal of an action potential generated in a sinoatrial node near the right atrium is sequentially transmitted to the entire heart by the impulse conducting system, and the electrical signal causes contraction of the myocardium. Therefore, information about the beating of the heart can be measured by observing the fluctuation of the electric potential of the heart caused by the conduction of the electric signal. Since the two electrodes 82 are in contact with each other on the left and right sides of the chest of the laborer Wi so as to sandwich the heart, fluctuations in the heart potential can be observed from the electric potential difference between the two electrodes 82. Since the waveform of the fluctuation of the electric potential of the heart is usually a waveform that is regularly repeated with the beat of the heart, the heart rate, which is the number of beats of the heart per fixed time, can be measured from the waveform.

The acceleration sensor 922 measures the acceleration applied to the measuring device 9. As shown in FIG. 2, the measuring device 9 is located near the center of the chest of the laborer Wi when the laborer Wi wears the wear 81. Therefore, since the measuring device 9 also moves when the laborer Wi wearing the wearable device 8 moves his/her body, the acceleration sensor 922 can measure the acceleration of the laborer Wi with the body movement. In this embodiment, the value obtained by integrating the acceleration measured by the acceleration sensor 922 for a certain period of time is used as the amount of physical activity of the laborer Wi.

Two wirings 83 are connected to the input/output unit 93. The wirings 83 are provided with connectors that can be connected to the input/output unit 93 at the ends opposite to the electrodes 82, respectively, so that the wirings 83 are connected to the input/output unit 93 when the measuring device 9 is attached to the wear 81. The electric signal acquired by the two electrodes 82 is input to the measuring device 9 via the two wirings 83 and the input/output unit 93, and is used for measuring the heart rate by the heart rate sensor 921.

The identification code unit 94 holds an identification code that can identify each wearable device 8. In the present embodiment, since each wearable device 8 is attached to the laborer Wi, each wearable device 8 and the determination device 1 are communicably connected to each other, and the biological information of each laborer Wi measured by each wearable device 8 is input to the determination device 1, the identification code unit 94 of each wearable device 8 holds an identification code that can identify itself from the other wearable devices 8 so as to be able to identify from which wearable device 8 the biological information input to the determination device 1 has been input. The identification code used in the identification code unit 94 may be any number, character, or symbol as long as each wearable device 8 can be identified. For example, when ten wearable devices 8 are used, serial numbers from 1 to 10 may be assigned to them and used as identification codes, respectively.

The communication unit 95 wirelessly communicates various data with an external device. The measuring device 9 can wirelessly communicate various data with the determination device 1 via the communication unit 94. The communication unit 95 can be configured by using, for example, a wireless communication device conforming to a general wireless communication standard such as a wireless LAN or a mobile phone channel. The measuring device 9 and the determination device 1 may be directly wirelessly connected between the communication unit 95 and the communication unit 6 by matching the wireless communication standards between the communication unit 95 of the measuring device 9 and the communication unit 6 of the determination device 1. Alternatively, they may be connected via a network such as the Internet by using a router or the like.

The measuring device 9 may be configured by using, for example, Union Tool's heart rate sensor WHS-2 (WHS: registered trademark). Since the WHS-2 is equipped with a function for measuring heart rate information including heart rate and three-axis acceleration and a wireless communication function, the measuring device 9 can be easily configured by using the WHS-2.

In the present embodiment, as an example of the wearable device 8, a clothing-type wearable device worn on the upper body of the laborer Wi is shown, but not limited to that, it suffices that it is worn on the body of the laborer Wi and is able to acquire biological information including the heart rate of the laborer Wi during laboring. For example, as the wearable device 8, a wristband-type one worn on the wrist of the laborer Wi may be used to measure the heart rate by an optical heart rate sensor that measures the heart rate from the pulse of the wrist. Further, it is not necessary to measure all the necessary biological information with one wearable device 8. For example, when it is desired to measure the heart rate and the amount of physical activity as the biological information, two wearable devices may be worn: one is for measuring the heart rate, and another is for measuring the amount of physical activity.

According to the determination device 1 according to the present embodiment configured as described above, each laborer Wi is equipped with a wearable device 8, the wearable device 8 includes a measuring device 9, and the biological information measuring unit 92 of the measuring device 9 measures the heart rate and the amount of physical activity of the laborer Wi as biological information by the heart rate sensor 921 and the acceleration sensor 922. Each wearable device 8 includes an identification code unit 4 that holds an identification code that can identify itself from another wearable device 8 and a communication unit 95, and is communicably connected to the determination device 1 wirelessly via the communication unit 95. Each wearable device 8 associates the biological information measured by the biological information measuring unit 92 with the identification code held in the identification code unit 4 and transmits the biological information to the determination device 1 at regular intervals. The determination device 1 includes a communication unit 6 and is connected to each wearable device 8 via the communication unit 6 so as to be able to wirelessly communicate, and the biological information associated with the identification code transmitted from each wearable device 8 is, after being received by the communication unit 6, sent to the biological information acquisition unit 3. The biological information acquisition unit 3 acquires the biological information of each wearable device 8 that has been sent, and manages and holds the biological information of each wearable device 8 by the associated identification code. The biological information acquisition unit 3, when newly acquiring the biological information of any of the wearable devices 8, transmits the identification code of the wearable device 8 of the newly acquired biological information to the determination unit 5. The determination unit 5, when the identification code is sent from the biological information acquisition unit 3, refers to the latest biological information of the wearable device 8 corresponding to the sent identification code from the biological information of each wearable device 8 managed by the biological information acquisition unit 3, calls a model formula for discriminating the health risk due to the labor load corresponding to the biological information from the model formula storage unit 4, determines the health risk based on the biological information and the called model formula, and associates the determination result with the identification code and saves it. For example, each wearable device 8 may be provided with warning means such as a warning lamp, and when the determination result by the determination unit 5 is bad, the warning means may be configured so as to transmit a command to issue a warning to the warning means of the wearable device 8 of the identification code from the identification code associated with the determination result. As described above, according to the determination device 1, the health risk of each laborer can be determined only by measuring the biological information of each laborer Wi with the wearable device 8.

Here, the model formula stored in the model formula storage unit 4 will be described. The model formula stored in the model formula storage unit 4 is a model formula for discriminating the health risk due to the labor load of the laborer Wi based on the biological information of the laborer Wi acquired by the biological information acquisition unit 3. In the present embodiment, the biological information of the laborer Wi acquired by the biological information acquisition unit 3 is the heart rate and the amount of physical activity measured by the wearable device 8 attached to the laborer Wi. The labor load of laborer Wi is different depending on the laborer Wi because the physical ability of each laborer Wi is different even if the labor content is the same. Therefore, it is considered that the reserve heart rate (% of Heart Rate Reserve, % HRR) (hereinafter referred to as % HRR) that can estimate the labor load applied to the laborer Wi based on the heart rate, which is the biological information of the laborer Wi, can be used as a model formula. Here, assuming that the heart rate of the laborer Wi measured by the wearable device 8 is $x_{1i}$, the % HRR for the laborer Wi is expressed by the following formula (1).

[Number 1]

$$\% \ HRR = \frac{x_{1i} - RH_i}{MH_i - RH_i} \times 100 [\%] \quad (1)$$

In formula (1), $RH_i$ is the heart rate at rest of laborer Wi and $MH_i$ is the maximum heart rate of laborer Wi. However, if this formula (1) is to be used as a model formula stored in the model formula storage unit 4, since % HRR cannot be calculated only by the heart rate $x_{1i}$ of laborer Wi measured by the wearable device 8, it is necessary to measure the heart rate at rest RHi and the maximum heart rate MI-Ii of the laborer Wi in advance, and a model formula is prepared for each laborer Wi, data management is also complicated.

Therefore, the following formula (2) can be used as a model formula stored in the model formula storage unit 4.

[Number 2]

$$\% \ HRR = \frac{x_{1i} - ARH}{AMH - ARH} \times 100 [\%] \quad (2)$$

In formula (2), ARH is the laborer's heart rate at rest calculated from known sample data, and AMH is the laborer's maximum heart rate calculated from known sample data. Therefore, if formula (2) is used as a model formula, the % HRR of laborer Wi can be calculated by measuring the heart rate $x_{1i}$ of laborer Wi with the wearable device 8. In this case, the determination unit 5 calculates the % HRR of the laborer Wi by the formula (2), and can determine the health risk due to the labor load of laborer Wi in such a manner that it determines that there is a health risk if the % HRR is equal to or more than a certain reference value, and determines that there is no health risk if it is less than the reference value. As the reference value of % HRR, which is the basis of this determination, 40% can be used with reference to Non-Patent Documents 1 to 3 and the like. The determination unit 5 may determine that if the % HRR<40%, there is no health risk, and if the % HRR≥40%, there is a health risk. In addition, instead of determining with two choices of presence or absence of health risk, the determination unit 5 may determine with three or more choices, such as determining with three choices in which % HRR<40% is low health risk, 40%≤% HRR<60% is medium health risk, and 60%≤% HRR is high health risk.

As known sample data used to calculate ARH and AMH in formula (2), pre-measured heart rate at rest and pre-measured maximum heart rate for laborers extracted from the population parameter of the laborer population including laborer Wi are preferably used. The number of elements of the sample to be extracted may be appropriately determined, and is preferably ten or more. ARH may use the average heart rate at rest of this known sample data, and AMH may use the average maximum heart rate of this known sample data. Since the maximum heart rate is the maximum critical heart rate and may be difficult to measure, a statistical formula for calculating the maximum heart rate from a commonly known age may be used. Several such formulas for calculating the maximum heart rate from an age are known, and for example, the following formula (3) can be used.

$$\text{Maximum heart rate} = 208 - \text{age} \times 0.7 \quad (3)$$

Therefore, it is possible to create the age data of the laborer extracted as known sample data and to calculate the AMH from the maximum heart rate calculated by formula (3).

As described above, although formula (2) can be used as a model formula stored in the model formula storage unit 4, since each individual laborer Wi has a different physical ability, when the error between the heart rate at rest RHi and the maximum heart rate MHi of the laborer Wi and the heart rate at rest ARH and the maximum heart rate AMH based on the sample data is large, the % HRR calculated by formula (2) may not be an appropriate value. In such a case, it is conceivable to predict the value of % HRR from known sample data by single regression analysis with the objective variable as % HRR and the explanatory variable as heart rate $x_1$, but in the case of single regression analysis, in some cases, the predicted % HRR value may be negative.

Therefore, in the present embodiment, logistic regression is used. Logistic regression is a kind of statistical regression model that follows the Bernoulli distribution, which is a discrete probability distribution that takes 1 for probability p and 0 for probability q=1−p. In logistic regression, the probability p that takes 1 is used as the objective variable, and the probability p that is the objective variable is predicted by the following formula (4) using j explanatory variables from $x_1$ to $x_j$.

[Number 3]

$$p = \frac{1}{1 + \exp\{-(b_0 + b_1 x_1 + b_2 x_2 + \ldots + b_j x_j)\}} \quad (4)$$

In formula (4), $b_0$ is a constant and $b_j$ is a partial regression coefficient, which is a parameter. As known sample data, for some samples, the measurement values of j explanatory variables from $x_1$ to $x_j$ measured respectively in advance, and data indicating to which of 1 and 0 the respective samples are classified based on a certain reference are created, and by using the known sample data, the parameters of $b_0$ and $b_1$ to $b_j$ can be estimated by the maximum likelihood method or the like. The formula obtained by applying $b_0$ and $b_1$ to $b_j$ estimated from the known sample data to formula (4) is used as the model formula. By doing so, for an unknown object, it is possible to predict the probability p of 1 by measuring from $x_1$ to $x_j$ and substituting the measured values into the model formula. Since the prediction result by logistic regression is a probability and always has a value between 0 and 1, it does not become unpredictable due to a negative value unlike the prediction result by single regression analysis of % HRR.

Here, since it is desired to obtain a model formula for determining the health risk due to the labor load of the laborer Wi by the determination unit 5, the model formula should be such that the probability p that becomes 1 with the health risk is predicted as the objective variable, with 1 as the case with the health risk, and 0 as the case without the health risk. For example, % HRR may be used as a reference for 1 with health risk and 0 without health risk. Here, 1 is discriminated if % HRR<40%, and 0 is discriminated if % HRR≥40%. The biological information measured by the wearable device 8 is used as the explanatory variable $x_j$. In this embodiment, since the heart rate and the amount of physical activity are measured by the wearable device 8, two explanatory variables are used with the heart rate as $x_1$ and the amount of physical activity as $x_2$. Then, the formula obtained by substituting the parameters of $b_0$, $b_1$ and $b_2$ estimated from the known sample data into the formula (4) can be used as the model formula stored in the model formula storage unit 4. The known sample data used to estimate the parameters of $b_0$, $b_1$ and $b_2$ here require the measurement data of heart rate and amount of physical activity used as explanatory variables for each sample, and the heart rate at rest and maximum heart rate for obtaining the % HRR used as a reference of 1 or 0 of health risk.

As described above, the determination unit 5 stores the model formula for predicting the probability p with a health risk from the biological information measured by the wearable device 8 obtained by the logistic regression in the model formula storage unit 4. Thereby, the determination unit 5 calculates the probability p with a health risk based on the biological information of the laborer Wi measured by the wearable device 8 and acquired by the biological information acquisition unit 3 and the model formula stored in the model formula storage unit 4, and can determine the health risk of laborer Wi in such a manner that it determines that there is a health risk when p≥0.5, and determines that there is no health risk when p<0.5.

The model formula calculated by the above logistic regression uses two pieces of biological information, the heart rate and the amount of physical activity of the laborer Wi, as the explanatory variables. However, the model formula may use only one piece of biological information, the heart rate of the laborer Wi as the explanatory variable, or may use three or more pieces of biological information as the explanatory variables when the biological information acquisition unit 3 acquires not only the heart rate and amount of physical activity of the laborer Wi, but also other examples such as blood pressure.

Further, the determination unit 5 may use only the model formula calculated by the logistic regression as described above as the model formula stored in the model formula storage unit 4, and determine the health risk from the one model formula. For example, the model formula of logistic regression and the model formula of % HRR such as formula (2) are stored in the model formula storage unit 4, and the determination unit 5 may be configured so as to determine the health risk by each of the two model formulas from the biological information of the laborer Wi, and if it is determined that there is a health risk in either one, determine that there is a health risk in the laborer Wi, and thus reducing determination omission of presence of health risk, or the determination may be made by using three or more model formulas.

Further, in the present embodiment, a model formula by binary logistic regression with no health risk as 0 and health risk as 1 is used based on % HRR=40%. However, by using polynomial logistic regression, a model formula that discriminates into three or more ranks may be calculated and used, for example, such as discriminating into three ranks in which if % HRR<40%, the health risk is low, 0, if 40%≤% HRR<60%, the health risk is medium, 1, and if 60%≤% HRR, the health risk is high, 2.

The following shows an example in which a model formula by logistic regression was actually obtained. Using 12 people with 8 scaffolders and 4 assistants laboring at the construction site as samples, each of the 12 people was equipped with a wearable device 8 to measure heart rate and amount of physical activity during labor at the construction site. Then, the heart rate and amount of physical activity were used as known sample data for obtaining a model formula. The heart rate and amount of physical activity were measured at 15 minute intervals and 294 datasets were obtained. The results are shown in Table 1 below. The unit of heart rate in Table 1 is bpm, which is the number of heartbeats per minute, and the unit of amount of physical activity is mG, which is the unit of acceleration based on 1G, which is the standard gravity. In Table 1, the estimated maximum heart rate is the value obtained from each age of 12 samples using formula (3), and the estimated heart rate at rest is the heart rate at rest measured at rest time. The % HRR was calculated for each dataset by formula (1) using the estimated maximum heart rate and the estimated heart rate at rest. Then, the data with % HRR<40% was classified as 0 without health risk, and the data with % HRR≥40% was classified as 1 with health risk. The results are shown in Table 2 below. As shown in Table 2, % HRR≥40% in this sample data, and the number of pieces of data classified as 1 with health risk was 36.1% of the total.

TABLE 1

| Samples | Estimated maximum heart rate | Estimated heart rate at rest | Average heart rate during laboring | Average heart rate throughout the day | Average % HRR throughout the day | Average amount of physical activity |
|---|---|---|---|---|---|---|
| Assistant 1 | 178 | 76 | 93.0 | 90.7 | 14.4 | 96.1 |
| Assistant 2 | 170 | 83 | 114.4 | 108.4 | 29.2 | 109.1 |
| Assistant 3 | 193 | 75 | 93.3 | 89.4 | 12.2 | 159.6 |
| Assistant 4 | 161 | 76 | 91.5 | 90.4 | 16.9 | 74.2 |
| Scaffolder 1 | 200 | 77 | 123.3 | 115.1 | 31.0 | 184.1 |
| Scaffolder 2 | 180 | 79 | 107.0 | 102.0 | 22.8 | 99.3 |
| Scaffolder 3 | 188 | 76 | 118.7 | 110.5 | 30.8 | 155.6 |
| Scaffolder 4 | 179 | 75 | 109.4 | 102.0 | 25.7 | 176.0 |
| Scaffolder 5 | 179 | 75 | 125.2 | 117.4 | 40.7 | 139.7 |
| Scaffolder 6 | 180 | 72 | 119.6 | 109.5 | 34.7 | 147.7 |
| Scaffolder 7 | 184 | 80 | 132.4 | 124.2 | 42.5 | 137.7 |
| Scaffolder 8 | 198 | 74 | 122.5 | 11.9 | 33.8 | 102.1 |

TABLE 2

| | Health risk | Frequency | Percentage |
|---|---|---|---|
| %HRR < 40% | 0 | 188 | 63.9 |
| 40% ≤ %HRR | 1 | 106 | 36.1 |

The results of logistic regression of 1 or 0 with health risk as the objective variable from this sample data are shown in Tables 3 and 4. Here, logistic regression was performed on three models, which are model 1 using only one explanatory variable of heart rate $x_1$, model 2 using two explanatory variables of heart rate $x_1$ and amount of physical activity $x_2$, and model 3 using three explanatory variables of BMI as $x_3$ in addition to heart rate $x_1$ and amount of physical activity $x_2$, and verification of the percentage of correct discrimination of health risk for the calculated model formula and the significance of the model and coefficient was performed. BMI is a body mass index, which is generally used as a measure of the degree of obesity, and is a numerical value calculated by the following formula (5).

$$BMI = weight \div (height)^2 [kg/m^2] \quad (3)$$

TABLE 3

| | Model 1 x1: Heart rate | Model 2 x1: Heart rate x2: Amount of physical activity | Model 3 x1: Heart rate x2: Amount of physical activity x3: BMI |
|---|---|---|---|
| Percentage of correct discrimination (%) | 93.5 | 97.3 | 96.6 |
| Number of parameters | 2 | 3 | 4 |

TABLE 3-continued

| | Model 1 x1: Heart rate | Model 2 x1: Heart rate x2: Amount of physical activity | Model 3 x1: Heart rate x2: Amount of physical activity x3: BMI |
|---|---|---|---|
| AIC | 58.42 | 52.86 | 50.87 |
| Significance of the model and coefficient | All significant | All significant | Coefficient was not significant |

TABLE 4

| | Heart rate | Amount of physical activity | BMI |
|---|---|---|---|
| Heart rate | — | 0.650** | −0.140* |
| Amount of physical activity | | — | 0.268 |
| BMI | | | — |

Significant correlations
***: <0.001
**<0.01
*<0.05

As can be seen from the results shown in Table 3, model 2 has a higher percentage of correct discrimination than model 1, and the verification results of the significance of the model and the coefficient are all significant. Even in model 1 in which only the heart rate is used as an explanatory variable, the percentage of correct discrimination is as high as 93.5%, and it is considered that it can be sufficiently used as a model formula to be stored in the model formula storage unit 4, but as in model 2, it is considered that a more accurate determination of health risk can be made by using the model formula calculated by using the amount of physical activity as an explanatory variable in addition to the heart rate in the model formula storage unit 4. In addition, it was found also from Table 4 that the possibility of multicollinearity between heart rate and amount of physical activity was low, and that the model formula based on heart rate and amount of physical activity could be effectively used. However, when BMI was added as an explanatory variable as in model 3, the percentage of correct discrimination decreased compared to model 2, and the result was that the coefficient was not significant. Therefore, the model formula calculated by the model 3 was determined to be unsuitable as the model formula used in the model formula storage unit 4. The model formula stored by the model formula storage unit 4 may use a model formula in which biological information other than the heart rate and amount of physical activity is used as an explanatory variable, but in that case, the explanatory variables are selected so that the percentage of correct discrimination becomes as high as possible and the model and coefficient are significant.

The model formula calculated by model 2 this time is shown in the following formula (6). It was estimated that $b_0=-71.60$, $b_1=0.624$, and $b_2=-0.018$.

[Number 4]

$$p = \frac{1}{1 + \exp\{-(-71.60 + 0.624x_{1i} - 0.018x_{2i})\}} \quad (6)$$

In formula (6), $x_{1i}$ is the heart rate of the laborer Wi acquired by the biological information acquisition unit 3, and $x_{2i}$ is the amount of physical activity of the laborer Wi acquired by the biological information acquisition unit 3. Therefore, by using formula (6) as a model formula to be stored in the model formula storage unit 4, if the heart rate and amount of physical activity of the laborer Wi are measured by the wearable device 8, without performing measurement or the like of other prior biological information, the determination unit 5 can calculate the probability p of being discriminated as 1 with a health risk from the measured heart rate and amount of physical activity of the laborer Wi by the formula (6), and from the result, determine the health risk of the laborer Wi in such a manner that when $p \geq 0.5$, it determines that there is a health risk, and when $p < 0.5$, it determines that there is no health risk.

DESCRIPTION OF REFERENCE SIGNS

1 Determination device
3 Biological information acquisition unit
4 Model formula storage unit
5 Determination unit
8 Wearable device
Wi Laborer

The invention claimed is:

1. A device for determining health risk of a laborer comprising:
  a wearable device, configured to be worn on the laborer's body, the wearable device having a heart rate sensor, an acceleration sensor, and a communication unit;
    the heart rate sensor configured to obtain heart rate information corresponding to a heart rate of the laborer;
    the acceleration sensor configured to obtain acceleration information corresponding to movement of the laborer;
    the communication unit configured to communicate the heart rate information and the acceleration information wirelessly; and
  a determination device, remote from the wearable device, configured to receive the heart rate information and the acceleration information wirelessly from the communication unit of the wearable device, the determination device having a biological information acquisition unit and a determination unit;
    the biological information acquisition unit configured to acquire biological information including the heart rate information from the heart rate sensor and the acceleration information from the acceleration sensor, and determine an amount of physical activity of the laborer based on the acceleration information acquired during a time period; and
    the determination unit configured to determine the health risk of the laborer based on the biological information of the laborer provided by the biological information acquisition unit, the determination unit performing processor-executed steps of:
      determining an at-rest heart rate of the laborer based on the biological information;
      determining a maximum heart rate of the laborer based on the biological information;
      determining a current heart rate of the laborer based on the biological information;
      determining, with a first model formula, a reserve heart rate of the laborer based on the at-rest heart rate, the maximum heart rate, and the current heart rate; and
      providing a warning indication corresponding to the health risk of the laborer;
    wherein the laborer is a first laborer of a plurality of laborers;
    wherein the determination unit is further configured to determine and store sample data corresponding to each of the plurality of laborers, the sample data including, for each of the plurality of laborers, the heart rate information and the amount of physical activity, and the reserve heart rate using the first model formula; and
    wherein providing the warning indication corresponding to the health risk of the first laborer further comprises:
      using logistic regression of the sample data to calculate a second model formula with the heart rate information and the amount of physical activity as explanatory variables: and
      providing the warning indication corresponding to the health risk based on a result of the second model formula,
    wherein providing the warning indication corresponding to the health risk of the first laborer further comprises providing the warning indication based on the reserve heart rate of the first laborer from the first model formula even though the result of the second model formula does not indicate a health risk.

2. The device according to claim 1, wherein, in providing the warning indication, the warning indication is communicated to the first laborer via a component carried by the wearable device.

3. The device according to claim 1, wherein:
  the wearable device is a first wearable device associated with the first laborer; and
  the device further comprises a plurality of wearable devices, each of which is associated with a corresponding one of the plurality of laborers.

4. The device according to claim 3, wherein each of the plurality of wearable devices is configured as a shirt.

5. The device according to claim 4, wherein each of the plurality of wearable devices communicates with the determination device.

6. The device according to claim 1, wherein:
  the wearable device is configured as a shirt; and
  the heart rate sensor has a first electrode and a second electrode.

7. The device according to claim 1, wherein:
the device further comprises a plurality of wearable devices, each of which is associated with a corresponding one of the plurality of laborers;
each of the plurality of wearable devices is configured as a shirt; and
each of the plurality of wearable devices communicates with the determination device.

8. The device according to claim 1, wherein the first model formula is represented by the equation:

$$\text{reserve heart rate} = (\text{current heart rate} - \text{at-rest heart rate})/(\text{maximum heart rate} - \text{at-rest heart rate}).$$

9. The device according to claim 1, wherein the sample data includes at-rest heart rate data and maximum heart rate data pre-measured for the plurality of laborers.

* * * * *